(12) United States Patent
Goto et al.

(10) Patent No.: US 6,383,645 B1
(45) Date of Patent: May 7, 2002

(54) GLASS-CERAMIC SUBSTRATE FOR AN INFORMATION STORAGE MEDIUM

(75) Inventors: Naoyuki Goto; Junko Ishioka; Yasuyuki Kawashima, all of Sagamihara (JP)

(73) Assignee: Kabushiki Kaisha Ohara, Kanagawa-ken (JP)

( * ) Notice: Subject to any disclaimer, the term of this patent is extended or adjusted under 35 U.S.C. 154(b) by 0 days.

(21) Appl. No.: 09/260,768

(22) Filed: Mar. 2, 1999

Related U.S. Application Data

(63) Continuation of application No. 09/260,468, filed on Mar. 2, 1999.

(30) Foreign Application Priority Data

Mar. 23, 1998 (JP) ............................................ 10-094020
Apr. 20, 1998 (JP) ............................................ 10-125316
Dec. 10, 1998 (JP) ............................................ 10-351682

(51) Int. Cl.[7] ........................ B32B 17/06; C03C 3/085; G11B 5/84
(52) U.S. Cl. .................. 428/426; 428/64.3; 428/64.4; 428/65.6; 428/65.7; 428/694 SG; 428/900; 501/4; 501/68; 501/69; 501/72
(58) Field of Search ................ 428/426, 64.1, 428/64.2, 64.4, 65.3, 65.6, 65.7, 65.5, 64.3, 432, 694 SG, 900; 501/63, 68, 66, 69, 72, 136, 4, 7

(56) References Cited

U.S. PATENT DOCUMENTS 4,480,044 A * 10/1984 McAlinn
5,494,721 A * 2/1996 Nakagawa et al.
5,567,217 A * 10/1996 Goto et al.
5,580,363 A 12/1996 Goto et al.
5,626,935 A 5/1997 Goto et al.
5,972,460 A * 10/1999 Tachiwana
5,997,977 A * 12/1999 Zou et al.

FOREIGN PATENT DOCUMENTS

| EP | 0781 731 A1 | 2/1997 |
| EP | 0779612 | 6/1997 |
| EP | 0788093 | 8/1997 |
| EP | 0810586 | 12/1997 |
| EP | 0875886 | 11/1998 |
| EP | 0917135 | 5/1999 |

OTHER PUBLICATIONS

Patents Abstracts of Japan, vol. 097, No. 006, #09035234 Feb. 7, 1997.
Patents Abstracts of Japan, vol. 011, No. 268, #62072547 Apr. 3, 1987.
European Search Report, The Hague, Aug. 17, 1999, Examiner Heywood, C.

* cited by examiner

*Primary Examiner*—Deborah Jones
*Assistant Examiner*—Jennifer McNeil
(74) *Attorney, Agent, or Firm*—Hedman & Costigan, P.C.

(57) ABSTRACT

There is provided a glass-ceramic substrate for an information storage medium usable in an information storage device of the ramp loading system. The glass ceramic substrate has a Young's modulus (GPa)/specific gravity of 37 or over and includes 5.3 to 8 weight percent (expressed on an oxide basis) of $Al_2O_3$. The glass ceramic substrate has, as its predominant crystal phases, lithium disilicate ($Li_2O \cdot 2SiO_2$) and α-quartz (α-$SiO_2$), has a coefficient of thermal expansion within a range from $65 \times 10^{-7}/°C$. to $130 \times 10^{-7}/°C$. within a temperature range from $-50°$ C. to $+70°$ C. and has a surface roughness (Ra) (arithmetic mean roughness) of 9 Å or below.

11 Claims, No Drawings

GLASS-CERAMIC SUBSTRATE FOR AN INFORMATION STORAGE MEDIUM

The present application is a continuation of 09/260,768 filed Mar. 2, 1999 and claims priority to Japanese Application Nos. 94020/1998 filed Mar. 23, 1998, 125316/1998, filed Apr. 20, 1998, and 351682, filed Dec. 10, 1998.

BACKGROUND OF THE INVENTION

This invention relates to a glass-ceramic substrate for an information storage medium and, more particularly, to a glass-ceramic substrate for an information storage medium such as a magnetic disk made of a glass-ceramic having improved super flatness of a surface of the substrate, a high Young's modulus and a low specific gravity capable of coping properly with a high speed rotation, and a range of coefficient of thermal expansion matching with coefficients of thermal expansion of constituent elements of the information storage medium. The invention relates also to a method for manufacturing the same and also to an information storage medium using this glass-ceramic substrate. In this specification, the term "information storage medium" means an information storage medium in the form of a disk and includes fixed type hard disks, removable type hard disks and card type hard disks used respectively for so-called "hard disks" for personal computers and storage of information in a network and other information storage medium in the form of a disk which can be used for storage of data in, e.g., digital video cameras and digital cameras.

Recent development of personal computers for multimedia purposes and digital video cameras and digital cameras which requires handling of a large amount of data has necessitated a magnetic information storage device of a large recording capacity. As a result, for increasing the recording density, there is a growing tendency in a magnetic information storage medium toward increasing in bit and track density and reducing the size of a bit cell. In conformity with the reduction in the size of the bit cell, a magnetic head performs its operation in closer proximity to the surface of a disk. As the magnetic head performs its operation in a near-contact state or contact state against the disk surface, technical development of a landing zone system has become important as a technique for starting and stopping a magnetic head. According to this system, a sticking prevention processing such as texturing is made in a specific zone of a disk (e.g., a radially inward or outward unrecorded portion of a disk) and starting and stopping of the magnetic head are performed in this zone which is called "landing zone".

In the current magnetic information storage device, the CSS (contact start stop) system is generally employed according to which a magnetic head is in contact with a surface of a magnetic information storage medium before starting and is lifted from the surface of the medium when the head has started its operation. If the surface of the medium on which the magnetic head contacts is exceedingly of a mirror surface, stiction takes place between the surface of the medium and the magnetic head with resulting difficulty in smooth starting of rotation of the medium due to increased friction and occurrence of damage to the surface of the medium. Thus, a substrate for a magnetic information storage medium must satisfy two conflicting requirements for a lower glide height of a magnetic head accompanying increased storage capacity and prevention of sticking of the magnetic head on the surface of the medium. For satisfying these conflicting requirements, the landing zone system has been developed and, aside from the landing zone system, development of a ramp loading system is under way according to which a magnetic head is completely in contact with the surface of a medium except for starting and stopping of the magnetic head when the magnetic haed is moved away from the surface of the medium. Accordingly, a current requirement for a substrate for a magnetic information storage medium is a smoother surface.

A technical development is under way for a higher speed transfer of information by a higher speed rotation of a magnetic information storage medium used for a magnetic information storage device. As the number of revolution of a medium increases, deflection and deformation of the medium occur and this gives rises to a requirement for a higher Young's modulus. Further, in addition to the conventional fixed type hard disks, information storage media such as a removable type hard disks and card type hard disks have been proposed and put into practice and application of digital video cameras and digital cameras for various uses have been started.

Known in the art of magnetic disk substrate materials is aluminum alloy. The aluminum alloy substrate, however, has projections or spot-like projections and depressions on the substrate surface during polishing due to various defects of the material and, therefore, is not sufficient as a substrate for a high recording density storage medium in flatness and smoothness. Besides, since aluminum alloy is a soft material and has a low Young's modulus and surface hardness, vibration of the substrate takes place during a high speed rotation of the medium with resulting deformation of the medium. Difficulty also arises in making the information storage medium thinner. Further, damage of the medium by contact with a head is liable to occur. Thus, the aluminum alloy substrate cannot sufficiently cope with the requirements for a high speed recording.

As materials for overcoming the above problems of the aluminum alloy substrate, known in the art are chemically tempered glasses such as soda-lime glass ($SiO_2$—CaO—$Na_2O$) and alumino-silicate glass ($SiO_2$—$Al_2O_3$—$Na_2O$). These materials, however, have the following disadvantages: (1) Since polishing is made after the chemical tempering process, the chemically tempered layer is seriously instable in making the disk thinner. (2) Since the glass contains $Na_2O$ as an essential ingredient, the glass has the problem that the film forming characteristics of the medium is deteriorated and, for preventing diffusion of $Na_2O$, it becomes necessary to apply a barrier coating over the entire surface of the substrate. This prevents stable production of the product at a competitive cost.

Aside from the aluminum alloy substrate and chemically tempered glass substrate, known in the art are som glass-ceramic substrates. For example, the glass-ceramics of a $SiO_2$—$Li_2O$—MgO—$P_2O_5$ system disclosed in U.S. Pat. No. 5,626,935 containing lithium disilicate ($Li_2O.2SiO_2$) and α-quartz (α-$SiO_2$) as main crystal phases is an excellent material as a material textured over the entire surface in which, by controlling the grain diameter of globular crystal grains of α-quartz, the conventional mechanical texturing or chemical texturing can be omitted and the surface roughness after polishing (Ra) can be controlled within a range from 15 Å to 50 Å. This glass-ceramic, however, cannot sufficiently cope with the requirement for the low glide height necessitated by the rapidly increasing recording density which requires the surface roughness (Ra) of 9 Å or below, preferably 6 Å or below. Further, no discussion or suggestion about a coefficient for thermal expansion has been made in this patent.

Japanese Patent Application Laid-open Publication No. Hei 9-35234 discloses a magnetic disk substrate made of a glass-ceramic of a $SiO_2$—$Al_2O_3$—$Li_2O$ system having predominant crystal phases of lithium dislicate ($Li_2O.2SiO_2$) and β-spodumene ($Li_2O.Al_2O_3.4SiO_2$). This glass-ceramic has a composition which contains a relatively large amount of $Al_2O_3$ ingredient and in which growth of $SiO_2$ crystals such as α-quartz (α-$SiO_2$) and α-cristobalite (α-$SiO_2$) is extremely restricted. The center line mean surface roughness of this glass-ceramic after polishing is defined as 20 Å or below but the center line mean surface roughness disclosed in examples is a rough one of 12 Å–17 Å which fails to reach the above described desired surface roughness and, therefore, this glass-ceramic cannot cope sufficiently with the requirement for the low glide height of a magnetic head. Further, since this glass-ceramic requires a high temperature of 820° C. to 920° C. for crystallization which prevents a large scale production of the product at a competitive cost.

International Publication WO97/01164 which includes the above described Japanese Patent Application Laid-open Publication No. Hei 9-35234 discloses a glass-ceramic for a magnetic disk in which the lower limit of the $Al_2O_3$ ingredient is lowered and temperature for crystallization is reduced (680° C.–770° C.). A sufficient improvement however cannot be achieved by merely lowering the lower limit of the $Al_2O_3$ ingredient. Besides, crystals grown in all examples disclosed are β-eucriptite ($Li_2O.Al_2O_3.2SiO_2$).

It is, therefore, an object of the invention to eliminate the above described disadvantages of the prior art and provide a glass-ceramic substrate for an information storage medium having an excellent sufrace characteristic capable of coping with the ramp loading system (i.e., contact recording of a magnetic head) for a high density recording, having an improved relation between Young's modulus and specific gravity by which the medium can stand a high speed rotation without causing vibration, and having a coefficient of thermal expansion which matches with coefficients of thermal expansion of component parts of the medium.

It is another object of the invention to provide a method for manufacturing the glass-ceramic substrate.

It is another object of the invention to provide an information storage medium employing this glass-ceramic substrate.

SUMMARY OF THE INVENTION

Accumulated studies and experiments made by the inventors of the present invention for achieving the above described objects of the invention have resulted in the finding, which has led to the present invention, that, in glass-ceramics having, as their predominant crystal phases, lithium disilicate ($Li_2O.2SiO_2$) and α-quartz (α-$SiO_2$), a glass-ceramic can be obtained which is advantageous over the prior art glass-ceramics for an information storage medium in that it has fine globular crystal grains and therefore has an excellent processability, has a smoother surface after polishing, has a coefficient of thermal expansion matching with coefficients of thermal expansion of component parts of the medium and has a high Young's modulus and a low specific gravity capable of coping with a high speed rotation of the medium. It has been found that the glassceramic substrate for an information storage medium achieving the object of the invention is particularly useful for the ramp loading system owing to its superflatness.

For achieving the above described object of the invention, there is provided a glass-ceramic substrate for an information storage medium having Young's modulus (GPa)/specific gravity of 37 or over and comprising 5.8 to less than 10 weight percent (expressed on oxide basis) of $Al_2O_3$.

In one aspect of the invention, the Young's modulus is within a range from 95 GPa to 120 GPa and the specific gravity is within a range from 2.4 to 2.6.

In another aspect of the invention, a coefficient of thermal expansion is within a range from $65\times10^{-7}$/° C. to $130\times10^{-7}$/° C. within a temperature range from −50° C. to +70° C.

In another aspect of the invention, a surface roughness Ra (arithmetic mean roughness) after polishing is 9 Å or below.

In another aspect of the invention, predominant crystal phases are lithium disilicate ($Li_2O.2SiO_2$) and α-quartz (α-$SiO_2$).

In another aspect of the invention, the glass-ceramic substrate is substantially free of $Na_2O$ and PbO.

In another aspect of the invention, crystal grains of the crystal phases are fine globular grains.

In another aspect of the invention, an average diameter of crystal grains of crystal phases is 0.30 μm or below.

In another aspect of the invention, the glass-ceramic substrate comprises 0.3 weight percent or over (expressed on the basis of composition of the oxide) of MgO.

In another aspect of the invention, the glass-ceramic substrate has a composition which consists in weight percent expressed on the basis of composition of oxides of:

| | |
|---|---|
| $SiO_2$ | 71–81% |
| $Li_2O$ | 8–11% |
| $K_2O$ | 0–3% |
| MgO | 0.3–2% |
| ZnO | 0–1% |
| $P_2O_5$ | 1–3% |
| $ZrO_2$ | 0.5–5% |
| $TiO_2$ | 0–3% |
| $Al_2O_3$ | 5.3–8% |
| $Sb_2O_3$ | 0.1–0.5% |
| $SnO_2$ | 0–5% |
| $MoO_3$ | 0–3% |
| NiO | 0–2% |
| CoO | 0–3% |
| $Cr_2O_3$ | 0–3% | and having, as predominant crystal phases, lithium disilicate ($Li_2O.2SiO_2$) and α-quartz (α-$SiO_2$).

In another aspect of the invention, there is provided a glass-ceramic substrate for an information storage medium having, as its predominant crystal phases, lithium disilicate ($Li_2O.2SiO_2$) and α-quartz (α-$SiO_2$) which have fine globular crystal grains and having a surface roughness Ra (arithmetic mean roughness) after polishing of 9 Å or below.

In another aspect of the invention, there is provided a method for manufacturing the glass-ceramic substrate for an information storage medium which comprises steps of melting glass materials, forming molten glass, annealing formed glass and then heat treating the formed glass for nucleation under nucleation temperature within a range from 550° C. to 650° C. for one to twelve hours and further heat treating the formed glass for crystallization under cyrstallization temperature within a range from 680° C. to 800° C. for one to twelve hours and polishing the glass-ceramic to a surface roughness (Ra) of 9 Å or below.

In still another aspect of the invention, there is provided an information storage medium provided by forming a magnetic film and, if necessary, other layers including an undercoat layer, a protective layer and a lubricating layer, on the above described glass-ceramic substrate.

DETAILED DESCRIPTION OF THE INVENTION

Reasons for limiting the physical properties, surface characteristics, predominant crystal phases and crystal grain diameter, and composition will now be described. The composition of the glass-ceramic is expressed on the basis of composition of oxides as in their base glass.

Description will be made first about Young's modulus and specific gravity.

As described previously, there is a growing tendency toward a high speed rotation of an information storage medium for improving the recording density and data transfer speed. For coping with this tendency, a substrate material must have high rigidity and low specific gravity for preventing vibration of a disk caused by deflection during a high speed rotation. Further, in the case where the medium is used for uses where a magnetic head comes in contact with the medium or where the medium is used for a portable type device such as a removable type storage device, the substrate material must have sufficient mechanical strength, Young's modulus and surface hardness to be adapted for such uses.

It has been found that, if a substrate has a high rigidity but a large specific gravity, deflection of the disk occurs during a high speed rotation due to its large weight with the result that vibration of the disk occurs. Conversely, if the substrate has a low specific gravity but a low rigidity, vibration of the disk likewise occurs. Accordingly, there must be a balance between apparently conflicting properties of a high rigidity and a low specific gravity. It has been found that a proper range of Young's modulus (GPa)/specific gravity is 37 or over, preferably, 39 or over, more preferably 41 or over and, most preferably, 43 or over. It has also been found that there is a preferred range of rigidity. Even if the above ratio is satisfied with a low specific gravity, Young's modulus of at least 95 GPa is preferable from the standpoint of preventing vibration of the disk. Having regard to processability of the substrate and increase in the weight of the substrate, the upper limit of Young's modulus of the substrate preferably is 120 GPa. As to specific gravity, having regard to prevention of vibration, the substrate should preferably have specific gravity of 2.6 or below even if the substrate has a high rigidity. If specific gravity is below 2.4, a substrate having a desired rigidity cannot be substantially obtained in glass-ceramics of this glass system. Accordingly, Young's modulus (GPa)/specific gravity preferably is 50 or below.

Description will now be made about a coefficient of thermal expansion. As the recording density increases, positioning of the magnetic head relative to the information storage medium requires a high precision and, therefore, a high precision size is required for the substrate and respective component parts for the medium. Therefore, an influence of difference in the coefficient of thermal expansion between the substrate and the component parts for the medium cannot be ignored and difference in the coefficient of thermal expansion must be reduced to the maximum extent possible. As component parts for a small size magnetic information storage medium, ones having a coefficient of thermal expansion in a range from $+90 \times 10^{-7}/°$ C. to $+100 \times 10^{-7}/°$ C. are frequently used so that the substrate needs to have a coefficient of thermal expansion of the same order. There is a case, however, where a drive maker employs a component part made of a material which has a coefficient of thermal expansion which is out of the above described range, i.e., a coefficient of thermal expansion within a range from about $+70 \times 10^{-7}/°$ C. to about $+125 \times 10^{-7}/°$ C. For this reason, in the crystal system of the present invention, a range of coefficient of thermal expansion has been determined so that the substrate will be applicable to as wide a variety of materials of component parts as possible while having sufficient regard to the strength of the substrate. It has been found that the coefficient of thermal expansion should preferably be within a range from $+65 \times 10^{-7}/°$ C. to $+130 \times 10^{-7}/°$ C. within a temperature range from $-50°$ C. to $+70°$ C. A more preferable range of the coefficient of thermal expansion within the same temperature range is from $+95 \times 10^{-7}/°$ C. to $+110 \times 10^{-7}/°$ C.

Description will now be made about the crystal grain diameter of the predominant crystal phases and the surface characteristics of the substrate.

As described previously, as the recording density of the information storage medium increases, the glide height of the magnetic head is extremely reduced to 0.025 μm or below and the near contact recording system or the contact recording system has been developed. For coping with such tendency, the medium must have a more flat surface than the prior art disks. If one attempts to perform high recording density inputting and outputting of information on a magnetic information storage medium having a surface of the prior art flatness, proper inputting and outputting of a magnetic signal cannot be achieved because distance between the magnetic head and the medium is too large. If this distance is reduced, collision of the magnetic head against the surface of the medium occurs with resulting damage to the head or medium. For preventing occurrence of damages to the head and medium notwithstanding the extremely low glide height or the contact recording, the surface roughness (Ra) of the substrate should preferably be 9 Å or below, and more preferably 6 Å or below. For the same reason, a maximum surface roughness (Rmax) of the substrate should preferably be 100 Å or below, and more preferably 72 Å or below.

For obtaining a glass-ceramic substrate having such flatness, the shape and diameter of grown crystal grains become important factors. For processability and surface roughness of the substrate, the grown crystal grains should preferably be fine globular grains. More specifically, the crystal grains should preferably have an average diameter of 0.30 μm or below, or more preferably 0.2 μm or below, for achieving the desired surface roughness. For obtaining the desired Young's module, the crystal grains should preferably have an average diameter of 0.05 μm or over.

For realizing the above described physical properties, coefficient of thermal expansion and surface roughness, it has been found that the combination of lithium disilicate ($Li_2O \cdot SiO_2$) and α-quartz (α-$SiO_2$) as predominant crystal phases is the best combination.

As regards $Na_2O$, if the substrate contains this ingredient, diffusion of Na ion into the magnetic film occurs during the film forming process and this makes the magnetic film grains to become coarse and deteriorates orientation. The substrate must therefore be substantially free of this ingredient. The substrate should also be free of PbO which is undesirable from the standpoint of environment protection.

Additionally, a substrate for an information storage medium is required to be free from defects such as crystal unisotropy, foreign matters and impurities and have a fine and uniform texture. Such requirements are satisfied by providing the predominant crystal phases (lithium disilicate and α-quartz) having the above described crystal shape and diameter.

Reasons for limiting the composition range of the base glass as defined in the claims will now be described.

The $SiO_2$ ingredient is a very important ingredient for growing lithium disilicate ($Li_2O.2SiO_2$) and α-quartz (α-$SiO_2$) as predominant crystal phases by heat treating the base glass. If the amount of this ingredient is below 71%, grown crystals of the glass-ceramic becomes instable and its texture tends to become coarse. If the amount of this ingredient exceeds 81%, difficulty arises in melting and forming of the glass.

The $Li_2O$ ingredient is a very important ingredient for growing lithium disilicate ($Li_2O.2SiO_2$) as a predominant crystal phase by heat treating the base glass. If the amount of this ingredient is below 8%, difficulty arises in growing of this crystal phase and also in melting of the base glass. If the amount of this ingredient exceeds 11%, the grown crystal is instable and its texture tends to become coarse and its chemical durability is deteriorated.

The $K_2O$ ingredient improves the melting property of the glass and prevents the grown crystal from becoming too coarse. The amount of up to 3% of this ingredient will suffice.

The MgO and ZnO ingredients are effective for stabilizing the process of growth of the lithium disilicate ($L_2O.2SiO_2$) crystal growing as a predominant crystal phase and preventing growth of α-cristobalite (α-$SiO_2$) crystal which adversely affects mechanical and thermal characteristics of the glass-ceramic of the present invention. If the amount of the MgO ingredient is below 0.3%, these effects cannot be achieved. If the amount of the MgO ingredient exceeds 2% or the amount of the ZnO ingredient exceeds 1%, the product obtained will be instable and its texture will become too coarse.

The $P_2O_5$ ingredient is indispensable as a nucleating agent. If the amount of this ingredient is below 1%, growth of nucleus will become insufficient with resulting abnormal growth of crystals. If the amount of this ingredient exceeds 3%, opaque devitrification will take place in the base glass.

The $ZrO_2$ and $TiO_2$ ingredients are important ingredients which, in addition to the function, like the $P_2O_5$ ingredient, as nucleating agents, are effective for making the grown crystals fine, improving the mechanical strength and improving chemical durability. If the amount of the $ZrO_2$ ingredient is below 0.5%, these effects cannot be achieved. If the amount of the $ZrO_2$ ingredient exceeds 5% or the amount of the $TiO_2$ ingredient exceeds 3%, difficulty arises in melting of the base glass and $ZrSiO_4$ and the like slug are left unmelted.

The $Al_2O_3$ ingredient is effective for improving chemical durability and mechanical strength of the glass-ceramic. The type of grown crystal differs depending upon conditions of heat treatment. Having regard to various conditions of heat treatment, the amount of this ingredient should be below 10% for growing lithium disilicate ($Li_2O.2SiO_2$) and α-quartz. A preferable range of this ingredient is 5.3–8%.

The $Sb_2O_3$ ingredient is added as a refining agent in melting the base glass. If the amount of this ingredient is below 0.1%, this effect cannot be achieved. The addition of this ingredient up to 0.5% will suffice.

The $SnO_2$ and $MoO_3$ ingredients are effective as coloring agents of the glass-ceramic. These ingredients are particularly effective for detecting surface defects of the products. These ingredients may also be added for facilitating absorption of LD excited laser (Nd:YAG and other) used for texturing of a landing zone on a disk. These ingredients have an excellent translucency in the glass state and therefore addition of these ingredients facilitate examination of materials before crystallization. The ingredients also colorize the glass-ceramic in its crystallization process. It will suffice if the amount of the $SnO_2$ ingredient up to 5% is added and the amount of the $MoO_3$ ingredient up to 3% is added.

The NiO, CoO, $Cr_2O_3$ ingredients are effective, like the $SnO_2$ and $MoO_3$ ingredients, for improving absorption of LD excited laser (Nd:YAG and other) used for texturing of a landing zone on a disk. These ingredients, however, have no translucency in the glass state as the $SnO_2$ and $MoO_3$ ingredients. It will suffice if the amount of the NiO ingredient up to 2%, the amount of the CoO ingredient up to 3% and the amount of the $Cr_2O_3$ ingredient up to 3% are added respectively.

For manufacturing the glass-ceramic substrate for an information storage medium according to the invention, glass materials of the above described composition are melted and is subjected to a hot or cold forming process. The formed glass is subjected to heat treatment under a temperature within a range from 550° C. to 650° C. for one to twelve hours for nucleation and then is subjected to further heat treatment under a temperature within a range from 680° C. to 800° C. for one to twelve hours for crystallization.

Predominant crystal phases of the glass-ceramic obtained by the heat treatments are lithium disilicate ($Li_2O.2SiO_2$) and α-quartz (α-$SiO_2$) having globular crystal grains with a grain diameter of 0.05 μm or over and 0.30 μm or below.

The glass-ceramic then is lapped and polished in a conventional manner and the glass-ceramic substrate for an information storage medium having a surface roughness (Ra) of 3 Å–9 Å and Rmax of 100 Å or below is obtained.

EXAMPLES

Tables 1 to 3 show examples (No. 1 to No. 16) of compositions of the glass-ceramic substrate for an information storage medium made according to the invention together with the temperature of nucleation, temperature of crystallization, predominant crystal phases, crystal grain diameter (average), surface roughness (Ra) after polishing, Rmax, Young's modulus, specific gravity, Young's modulus (GPa)/specific gravity and coefficient of thermal expansion. Table 4 shows compositions and the above properties of the prior art $SiO_2$—$Li_2O$—MgO—$P_2O_5$ system glass-ceramic disclosed in U.S. Pat. No. 5,626,935 (Comparative Example 1) and the prior art $SiO_2$—$Al_2O_3$—$Li_2O$ system glass-ceramics disclosed in Japanese Patent Application Laid-open Publication No.Hei 9-35234 (Comparative Example 2) and International Publication No. WO97/01164 (Comparative Example 3).

TABLE 1

| | Examples | | | | |
|---|---|---|---|---|---|
| | 1 | 2 | 3 | 4 | 5 |
| $SiO_2$ | 75.3 | 75.5 | 77.2 | 77.5 | 74.3 |
| $Li_2O$ | 9.9 | 9.9 | 10.4 | 9.9 | 9.5 |
| $K_2O$ | 2.0 | 2.0 | | | 2.0 |
| MgO | 0.8 | 1.0 | 0.5 | 0.5 | 0.5 |
| ZnO | 0.5 | 0.5 | 0.5 | 0.5 | 0.5 |
| $P_2O_5$ | 2.0 | 2.0 | 2.0 | 1.8 | 2.0 |
| $ZrO_2$ | 2.3 | 2.3 | 2.6 | 2.6 | 2.0 |
| $TiO_2$ | | | | | |
| $Al_2O_3$ | 7.0 | 6.6 | 6.6 | 7.0 | 6.0 |
| $Sb_2O_3$ | 0.2 | 0.2 | 0.2 | 0.2 | 0.2 |
| $As_2O_3$ | | | | | |
| $SnO_2$ | | | | | 1.5 |
| $MoO_3$ | | | | | 1.5 |
| NiO | | | | | |

TABLE 1-continued

| | Examples | | | | |
|---|---|---|---|---|---|
| | 1 | 2 | 3 | 4 | 5 |
| CoO | | | | | |
| Cr$_2$O$_3$ | | | | | |
| Nucleation temperature (° C.) | 550 | 550 | 550 | 550 | 560 |
| Crytallization temperature (° C.) | 780 | 770 | 780 | 780 | 780 |
| Crystal phases and grain diameter (average) (μm) | LD 0.10 α-q 0.20 | LD 0.10 α-q 0.20 | LD 0.10 α-q 0.20 | LD 0.10 α-q 0.20 | LD 0.10 α-q 0.20 |
| Young's modulus (GPa) | 100 | 105 | 113 | 120 | 105 |
| Specific gravity | 2.47 | 2.48 | 2.50 | 2.52 | 2.48 |
| Young's modulus (GPa)/specific gravity | 40 | 42 | 45 | 48 | 42 |
| Surface roughness (Ra) | 7.0 | 8.0 | 7.5 | 6.0 | 7.3 |
| Maximum surface roughness (Rmax) | 79.0 | 83.0 | 80.4 | 72.0 | 81.2 |
| Coefficient of thermal expansion (10$^{-7}$/° C.) (−50° C.−+70° C.) | 110 | 100 | 119 | 123 | 115 |

TABLE 2

| | Examples | | | | |
|---|---|---|---|---|---|
| | 6 | 7 | 8 | 9 | 10 |
| SiO$_2$ | 73.5 | 71.3 | 71.3 | 71.0 | 73.8 |
| Li$_2$O | 10.0 | 10.0 | 10.0 | 11.0 | 9.9 |
| K$_2$O | 1.5 | 1.5 | 1.5 | 1.5 | 2.0 |
| MgO | 0.5 | 1.0 | 1.0 | 1.0 | 0.8 |
| ZnO | 0.5 | 0.5 | 0.5 | 0.5 | 0.5 |
| P$_2$O$_5$ | 2.0 | 2.0 | 2.0 | 2.0 | 2.0 |
| ZrO$_2$ | 1.5 | 2.0 | 2.0 | 2.0 | 2.8 |
| TiO$_2$ | 1.5 | 1.5 | 1.5 | 1.0 | |
| Al$_2$O$_3$ | 6.0 | 7.0 | 7.0 | 6.8 | 7.0 |
| Sb$_2$O$_3$ | 0.2 | 0.2 | 0.2 | 0.2 | 0.2 |
| As$_2$O$_3$ | | | | | |
| SnO$_2$ | | | 1.5 | 2.0 | |
| MoO$_3$ | | | 1.5 | 1.0 | |
| NiO | 0.5 | 0.5 | | | |
| CoO | 1.8 | 2.0 | | | |
| Cr$_2$O$_3$ | 0.5 | 0.5 | | | |
| Nucleation temperature (° C.) | 560 | 560 | 560 | 590 | 570 |
| Crystallization temperature (° C.) | 770 | 760 | 780 | 790 | 740 |
| Crystal phases and grain diameter (average) (μm) | LD 0.10 α-q 0.20 | LD 0.10 α-q 0.20 | LD 0.10 α-q 0.05 | LD 0.10 α-q 0.05 | LD 0.05 α-q 0.05 |
| Young's modulus (GPa) | 100 | 115 | 118 | 118 | 100 |
| Specific gravity | 2.54 | 2.54 | 2.53 | 2.48 | 2.47 |
| Young's modulus (GPa)/specific gravity | 39 | 45 | 47 | 48 | 40 |
| Surface roughness (Ra) | 5.5 | 6.3 | 5.3 | 5.0 | 3.0 |
| Maximum surface roughness (Rmax) | 63.0 | 76.0 | 53.0 | 51.0 | 32.0 |
| Coefficient of thermal expansion (10$^{-7}$/° C.) (−50° C.−+70° C.) | 98 | 100 | 105 | 108 | 95 |

TABLE 3

| | Examples | | | | | |
|---|---|---|---|---|---|---|
| | 11 | 12 | 13 | 14 | 15 | 16 |
| SiO$_2$ | 75.0 | 75.8 | 73.1 | 78.0 | 75.1 | 72.5 |
| Li$_2$O | 9.0 | 9.5 | 9.5 | 8.5 | 8.5 | 8.5 |
| K$_2$O | 2.5 | 1.0 | 0.5 | 0.5 | 1.0 | |
| MgO | 1.0 | 0.3 | 1.5 | 1.0 | 0.5 | 1.7 |
| ZnO | | | 0.7 | 1.0 | | 0.8 |
| P$_2$O$_5$ | 1.5 | 2.2 | 2.5 | 1.5 | 1.5 | 1.5 |
| ZrO$_2$ | 3.3 | 5.0 | 0.5 | 1.0 | 1.5 | 1.0 |
| TiO$_2$ | | | 0.5 | 0.5 | 1.0 | 2.5 |
| Al$_2$O$_3$ | 7.4 | 6.0 | 7.0 | 5.3 | 6.0 | 8.0 |
| Sb$_2$O$_3$ | 0.1 | 0.2 | 0.2 | 0.5 | 0.3 | 0.4 |
| As$_2$O$_3$ | 0.1 | | 0.2 | | 0.3 | 0.3 |
| SnO$_2$ | 0.1 | | 4.5 | | 0.3 | |
| MoO$_3$ | | | | | 3.0 | 2.8 |
| NiO | | | | | | |
| CoO | | | | 2.5 | | |
| Cr$_2$O$_3$ | | | | | | |
| Nucleation temperature (° C.) | 600 | 550 | 570 | 620 | 560 | 550 |
| Crystallization temperature (° C.) | 750 | 760 | 780 | 780 | 740 | 740 |
| Crystal phases and grain diameter (average) (μm) | LD 0.10 α-q 0.10 | LD 0.05 α-q 0.05 | LD 0.10 α-q 0.10 | LD 0.20 α-q 0.10 | LD 0.30 α-q 0.05 | LD 0.10 α-q 0.30 |
| Young's modulus (GPa) | 110 | 110 | 116 | 106 | 115 | 118 |
| Specific gravity | 2.46 | 2.46 | 2.56 | 2.51 | 2.49 | 2.48 |
| Young's modulus (GPa)/specific gravity | 45 | 45 | 45 | 42 | 46 | 48 |
| Surface roughness (Ra) | 5.0 | 3.0 | 4.5 | 3.5 | 3.0 | 7.0 |
| Maximum surface roughness (Rmax) | 56.0 | 29.0 | 51.0 | 45.0 | 25.0 | 88.0 |
| Coefficient of thermal expansion (10$^{-7}$/° C.) (−50° C.−+70°C.) | 115 | 95 | 100 | 100 | 96 | 130 |

TABLE 4

| | Comparative Examples | | |
|---|---|---|---|
| | 1 | 2 | 3 |
| SiO$_2$ | 69.0 | 76.1 | 76.0 |
| Li$_2$O | 9.0 | 11.8 | 10.0 |
| K$_2$O | 7.0 | 2.8 | 2.8 |
| MgO | 3.5 | | |
| ZnO | 0.5 | | |
| P$_2$O$_5$ | 1.5 | 2.0 | 2.0 |
| ZrO$_2$ | 1.0 | | |
| PbO | 1.5 | | |
| Al$_2$O$_3$ | 5.0 | 7.1 | 7.0 |
| BaO | 1.5 | | |
| Sb$_2$O$_3$ | | 0.2 | 0.2 |
| As$_2$O$_3$ | 0.5 | | |
| Nucleation temperature (° C.) | 450 | 500 | 450 |
| Crystallization temperature (° C.) | 760 | 850 | 750 |
| Crystal phases and grain diameter (average) (μm) | LD 0.10 α-q 0.60 | LD 0.10 β-spodumene 0.80 | LD 0.10 β-cristobalite 0.50 |
| Young's modulus (GPa) | 87 | 89 | 90 |
| Specific gravity | 2.43 | 2.53 | 2.48 |
| Young's modulus (GPa)/specific gravity | 36 | 35 | 36 |
| Surface roughness (Ra) | 15 | 17 | 10 |

TABLE 4-continued

|  | Comparative Examples | | |
|---|---|---|---|
|  | 1 | 2 | 3 |
| Maximum surface roughness (Rmax) | 180 | 230 | 124 |
| Coefficient of thermal expansion ($10^{-7}$/° C.) (−50° C.→+70° C.) | 64 | 60 | 64 |

TABLE 5

|  | Examples | | | | |
|---|---|---|---|---|---|
|  | 21 | 22 | 23 | 24 | 25 |
| $SiO_2$ | 76.4 | 75.2 | 72.5 | 75.6 | 78.0 |
| $Li_2O$ | 8.8 | 8.5 | 8.5 | 9.5 | 8.5 |
| $K_2O$ |  | 2.5 |  |  | 0.5 |
| MgO | 1.5 | 1.5 | 1.7 | 0.5 | 1.0 |
| ZnO |  | 0.5 | 0.8 | 0.3 | 0.7 |
| $P_2O_5$ | 1.3 | 2.5 | 1.5 | 2.5 | 1.5 |
| $ZrO_2$ | 4.2 | 0.7 | 1.0 | 4.5 | 1.0 |
| $TiO_2$ | 3.0 |  | 2.5 | 0.5 | 0.5 |
| $Al_2O_3$ | 4.5 | 4.0 | 8.0 | 4.5 | 5.3 |
| $Sb_2O_3$ | 0.3 | 0.3 | 0.4 | 0.1 | 0.5 |
| $As_2O_3$ |  | 0.3 | 0.3 | 0.5 |  |
| $SnO_2$ |  | 4.0 |  |  |  |
| $MoO_3$ |  |  | 2.8 |  |  |
| NiO |  |  |  | 1.5 |  |
| CoO |  |  |  |  | 2.5 |
| $Cr_2O_3$ |  |  |  |  |  |
| Nucleation temperature (° C.) | 580 | 600 | 550 | 570 | 620 |
| Crytallization temperature (° C.) | 750 | 800 | 740 | 760 | 780 |
| Crystal phases and grain diameter (average) (μm) | LD 0.05 α-q 0.10 | LD 0.10 α-q 0.10 | LD 0.10 α-q 0.30 | LD 0.20 α-q 0.05 | LD 0.20 α-q 0.10 |
| Young's modulus (GPa) | 118 | 100 | 118 | 115 | 106 |
| Specific gravity | 2.43 | 2.46 | 2.48 | 2.49 | 2.51 |
| Young's modulus (GPa)/specific gravity | 49 | 41 | 48 | 46 | 42 |
| Surface roughness (Ra) | 4.8 | 4.2 | 7.0 | 3.0 | 3.5 |
| Maximum surface roughness (Rmax) | 58.0 | 49.0 | 88.0 | 31.0 | 45.0 |
| Coefficient of thermal expansion ($10^{-7}$/° C.) (−50° C.→+70° C.) | 115 | 118 | 130 | 108 | 100 |

TABLE 6

|  | Examples | | | | |
|---|---|---|---|---|---|
|  | 26 | 27 | 28 | 29 | 30 |
| $SiO_2$ | 72.0 | 75.1 | 73.0 | 72.0 | 79.0 |
| $Li_2O$ | 8.5 | 8.5 | 10.5 | 10.8 | 8.5 |
| $K_2O$ | 2.5 | 1.0 | 1.0 | 2.7 | 1.5 |
| MgO | 0.9 | 0.5 | 0.5 | 1.0 | 0.5 |
| ZnO | 0.8 | 1.0 | 0.8 | 0.5 | 1.0 |
| $P_2O_5$ | 2.5 | 1.5 | 2.0 | 1.5 | 1.2 |
| $ZrO_2$ | 0.5 | 1.5 | 4.0 | 3.5 | 3.0 |
| $TiO_2$ |  | 1.0 | 1.0 |  |  |
| $Al_2O_3$ | 4.5 | 6.0 | 5.0 | 4.5 | 5.0 |
| $Sb_2O_3$ | 0.2 | 0.3 | 0.2 | 0.2 | 0.2 |
| $As_2O_3$ | 0.1 | 0.3 |  | 0.3 | 0.1 |
| $SnO_2$ | 5.0 | 0.3 |  |  |  |
| $MoO_3$ |  | 3.0 |  |  |  |
| NiO |  |  |  | 2.0 |  |
| CoO |  |  |  |  | 3.0 |
| $Cr_2O_3$ | 2.5 |  |  |  | 3.0 |
| Nucleation temperature (° C.) | 550 | 560 | 580 | 550 | 580 |
| Crytallization temperature (° C.) | 720 | 740 | 780 | 750 | 740 |
| Crystal phases and grain diameter (average) (μm) | LD 0.30 α-q 0.05 | LD 0.30 α-q 0.05 | LD 0.20 α-q 0.05 | LD 0.10 α-q 0.05 | LD 0.05 α-q 0.05 |
| Young's modulus (GPa) | 100 | 115 | 108 | 100 | 105 |
| Specific gravity | 2.58 | 2.49 | 2.46 | 2.47 | 2.44 |
| Young's modulus (GPa)/specific gravity | 39 | 46 | 44 | 40 | 43 |
| Surface roughness (Ra) | 3.0 | 3.0 | 3.0 | 3.2 | 3.8 |
| Maximum surface roughness (Rmax) | 28.0 | 25.0 | 36.0 | 33.0 | 42.0 |
| Coefficient of thermal expansion ($10^{-7}$/° C.) (−50° C.→+70° C.) | 98 | 96 | 97 | 98 | 96 |

TABLE 4

|  | Comparative Examples | | |
|---|---|---|---|
|  | 1 | 2 | 3 |
| $SiO_2$ | 69.0 | 76.1 | 76.0 |
| $Li_2O$ | 9.0 | 11.8 | 10.0 |
| $K_2O$ | 7.0 | 2.8 | 2.8 |
| MgO | 3.5 |  |  |
| ZnO | 0.5 |  |  |
| $P_2O_5$ | 1.5 | 2.0 | 2.0 |
| $ZrO_2$ | 1.0 |  |  |
| PbO | 1.5 |  |  |
| $Al_2O_3$ | 5.0 | 7.1 | 7.0 |
| BaO | 1.5 |  |  |
| $Sb_2O_3$ |  | 0.2 | 0.2 |
| $As_2O_3$ | 0.5 |  |  |
| Nucleation temperature (° C.) | 450 | 500 | 450 |
| Crytallization temperature (° C.) | 760 | 850 | 750 |
| Crystal phases and grain diameter (average) (μm) | LD 0.10 α-q 0.60 | LD 0.10 β-spodumene 0.80 | LD 0.10 β-cristobalite 0.50 |
| Young's modulus (GPa) | 87 | 89 | 90 |
| Specific gravity | 2.43 | 2.53 | 2.48 |
| Young's modulus (GPa)/specific gravity | 36 | 35 | 36 |
| Surface roughness (Ra) | 15 | 17 | 10 |
| Maximum surface roughness (Rmax) | 180 | 230 | 124 |
| Coefficient of thermal expansion ($10^{-7}$/° C.) (−50° C.→+70° C.) | 64 | 60 | 64 |

For manufacturing the glass-ceramic substrate of the above described examples, materials including oxides, carbonates and nitrates are mixed and molten in conventional melting apparatus at a temperature wtihin the range from about 1350° C. to about 1450° C. The molten glass is stirred to homogenize it and thereafter formed into a disk shape and annealed to provide a formed glass. Then, the formed glass is subjected to heat treatment to produce the crystal neclus under a temperature within the range from 550° C. to 650° C. for about one to twelve hours and then is further subjected to heat treatment for crystallization under a temperature within the range from 680° C. to 800° C. for about one to twelve hours to obtain a desired glass-ceramic. Then, this glass-ceramic is lapped with lapping grains having average grain diameter ranging from 5 μm to 30 μm for about 10 minutes to 60 minutes and then is finally polished with cerium oxide having grain diameter ranging from 0.5 μm to 2 μm for about 30 minutes to 60 minutes.

As shown in Tables 1 to 4, the glass ceramics of the present invention are different from the comparative examples of the prior art glass-ceramics in the predominant crystal phases and crystal grain diameter (average). In the glass ceramics of the present invention, crystal grains of lithium disilicate ($Li_2O.2SiO_2$) and α-quartz (α-$SiO_2$) are fine globular grains whereas the glass-ceramics of the Comparative Examples 1, 2 and 3 have a large grain diameter (average) of 0.5 μm or over. In view of the current tendency toward the super flatness, the glass ceramics of the comparative examples with this grain diameter will cause difficulties resulting from the surface roughness after polishing and falling off of crystal grains from the surface of the medium.

As regards Young's modulus, specific gravity and Young's modulus (Gpa)/specific gravity, the glass-ceramics of the present invention have excellent Young's modulus (Gpa)/specific gravity of 39 or over whereas the glass-ceramics of Comparative Examples 1, 2 and 3 have Young's modulus (Gpa)/specific gravity of less than 37 and therefore cannot sufficiently cope with a drive of a high speed rotation. Further, as regards the coefficient of thermal expansion, the glass-ceramics of the present invention have a coefficient of thermal expansion of $95 \times 10^{-7}$/° C. or over whereas the glass-ceramics of the Comparative Examples 1, 2 and 3 have a low coefficient of thermal expansion of $64 \times 10^{-7}$/° C. or below. Particularly, the glass-ceramics of Comparative Examples 2 and 3 contain β-spodumene and β-cristobalite which are crystal phases having a negative thermal expansion characteristic and, therefore, difference in the coefficient of thermal expansion between these glass-ceramics and the component parts of the drive device will become so great that these glass-ceramics are not suitable for a substrate for an information storage medium.

On the glass-ceramic substrates of the above described examples are formed films of a Cr middle layer (80 nm), a Co—Cr magnetic layer (50 nm) and a SiC protective layer (10 nm) by the DC sputtering method. Then, a perfluoropolyether lubricant (5 nm) is coated over the formed film to provide an information storage medium. The information storage medium thus obtained can reduce the glide height as compared to the prior art information storage medium owing to its excellent super flatness. Further, the information storage medium of the invention can be used for the information storage device of the ramp loading system in which the magnetic head performs inputting and outputting of signals in contact with the surface of the information storage medium without damaging the head or medium.

As described above, according to the present invention, there is provided a glass-ceramic substrate suitable for an information storage medium which has eliminated the disadvantages of the prior art substrates and has a flat surface characteristic capable of coping with a high recording density, has an excellent balance between a high Young's modulus and a low specific gravity suitable for a high speed rotation and a thermal expansion characteristic matching with one of an information storage medium drive device.

According to the invention, there are also provided a method for manufacturing the glass-ceramic substrate and an information storage medium using this substrate.

What is claimed is:

1. A glass-ceramic substrate for an information storage medium having a Young's modulus of GPa/specific gravity of 37 or over and comprising 5.3 to 8 weight percent, expressed on the basis of the oxide, of $Al_2O_3$.

2. A glass-ceramic substrate as defined in claim 1 wherein the Young's modulus is within a range of from 95 GPa to 120 GPa and the specific gravity is within a range of from 2.4 to 2.6.

3. A glass-ceramic substrate as defined in claim 1 wherein a coefficient of thermal expansion is within a range from $65 \times 10_{-7}$/° C. to $130 \times 10_{-7}$/° C. within a temperature range from $-50°$ C. to $+70°$ C.

4. A glass-ceramic substrate as defined in claim 1 wherein a surface roughness Ra, expressed as the arithmetic mean roughness, after polishing is 9 Å or below.

5. A glass-ceramic as defined in claim 1 which has crystal phases wherein the predominant crystal phases are lithium disilicate ($LiO.2SiO_2$) and α-quartz (α-$SiO_2$).

6. A glass-ceramic substrate as defined in claim 1 which is substantially free of $Na_2O$ and PbO.

7. A glass-ceramic substrate as defined in claim 1 wherein crystal grains of the crystal phases are fine globular grains.

8. A glass-ceramic substrate as defined in claim 1 wherein a average diameter of crystal grains of crystal phases is 0.30 μm or below.

9. A glass-ceramic substrate as defined in claim 1 comprising 0.3 weight percent or over, expressed on the basis of the oxide, of MgO.

10. A glass-ceramic substrate as defined in claim 1 having a composition which consist in weight percent expressed on the basis of the weight of the oxides of:

| | |
|---|---|
| $SiO_2$ | 71–81% |
| $LiO_2$ | 8–11% |
| $K_2O$ | 0–3% |
| MgO | 0.3–2% |
| ZnO | 0–1% |
| $P_2O_5$ | 1–3% |
| $ZrO_2$ | 0.5–5% |
| $TiO_2$ | 0–3% |
| $Al_2O_3$ | 5.3–8% |
| $Sb_2O_3$ | 0.1–0.5% |
| $SnO_2$ | 0–5% |
| $MnO_3$ | 0–3% |
| NiO | 0–2% |
| CoO | 0–3% |
| $Cr_2O_3$ | 0–3% | which has crystal phases and having, as predominant crystal phases, lithium disilicate ($Li_2O.2SiO_2$) and α-quartz (α-SiO2).

11. An information storage medium provided by forming a magnetic film and other layers including an undercoat layer, a protective layer and a lubricating layer, on a glass-ceramic substrate as defined in claim 1.

* * * * *

UNITED STATES PATENT AND TRADEMARK OFFICE
CERTIFICATE OF CORRECTION

PATENT NO.   : 6,383,645 B1
DATED        : May 7, 2002
INVENTOR(S)  : Naoyuki Goto et al.

It is certified that error appears in the above-identified patent and that said Letters Patent is hereby corrected as shown below:

Column 14,
Line 46, "$MnO_3$" should read -- $MoO_3$ --.

Signed and Sealed this

Twenty-second Day of November, 2005

JON W. DUDAS
*Director of the United States Patent and Trademark Office*